United States Patent [19]

Schroepfer, Jr. et al.

[11] Patent Number: 5,371,077
[45] Date of Patent: Dec. 6, 1994

[54] SIDE CHAIN DERIVATIZED 15-OXYGENATED STEROLS, METHODS OF USING THEM AND A PROCESS FOR PREPARING THEM

[75] Inventors: George J. Schroepfer, Jr.; Josef E. Herz; Shankar Swaminathan, all of Houston; William K. Wilson, Bellaire, all of Tex.

[73] Assignee: William Marsh Rice University, Houston, Tex.

[21] Appl. No.: 923,423

[22] Filed: Aug. 3, 1992

[51] Int. Cl.$^5$ .............................................. A61K 31/56
[52] U.S. Cl. ....................................... 514/179; 514/177; 514/178; 514/180; 514/182
[58] Field of Search ................. 552/540; 514/169, 177, 514/178, 179, 180, 182

[56] References Cited

U.S. PATENT DOCUMENTS 4,202,891  5/1980  Schroepfer, Jr. et al. ........... 514/178
4,900,477  2/1990  Dean et al. ............................ 514/179

OTHER PUBLICATIONS

S. Swaminathan et al., "Inhibitors of Sterol Synthesis. 3β,25-Dihydroxy-5α-cholest-8(14)-en-15-one, an Active Metabolite of 3β-Hydroxy-5α-cholest-8(14)-en-15-one," *J. Med. Chem.*, 35, 793-795 (1992).

J. E. Herz et al., "Inhibitors of Sterol Synthesis. A Highly Efficient and Specific Side Chain Oxidation of 3β-Acetoxy-5α-cholest-8(14)-en-15-one for Construction of Metabolites and Analogs of the 15-Ketosterol," *J. Lipid Res.*, 33(4), 579-598 (1992).

J. E. Herz et al., "Inhibitors of Sterol Synthesis. An Efficient and Specific Side Chain Oxidation of 3β-Hydroxy-5α-cholest-8(14)-en-15-one. Facile Access to its Metabolites and Analogs," *Tetrahedron Lett.*, 32(32), 3923-3926 (1991).

J. E. Herz et al., "Inhibitors of Sterol Synthesis. Synthesis and Spectral Properties of 3β-Hydroxy-24-dimethylamino-5α-chol-8(14)-en-15-one and its Effects on HMG-CoA Reductase Activity in CHO-K1 Cells," *Chem. Phys. Lipids*, 60, 61-69 (1991).

M. M. Kabat, "Synthesis of 26,27-Difluoro-25-hydroxy- and (25R,S)-27-Fluoro-25,26-Dihydroxy-cholesterol Derivatives from Methyl 3β-Hydroxy 5-Cholenate," *J. Fluorine Chem.*, 49, 207-215 (1990).

W.-Y. Huang et al. "Synthesis of Cholesterol and its Analogs with Fluorinated Side-Chains," *J. Fluorine Chem.*, 43, 305-318 (1989).

Primary Examiner—Johann Richter
Assistant Examiner—Kimberly J. Kestler
Attorney, Agent, or Firm—Finnegan, Henderson, Farabow, Garrett & Dunner

[57] ABSTRACT

Pharmaceutical compositions are provided for lowering the activity of HMG-CoA reductase and/or lowering serum cholesterol, comprising an amount effective to lower the activity of HMG-CoA reductase and/or lower serum cholesterol of a side chain derivatized 15-oxygenated sterol having the formula (I):

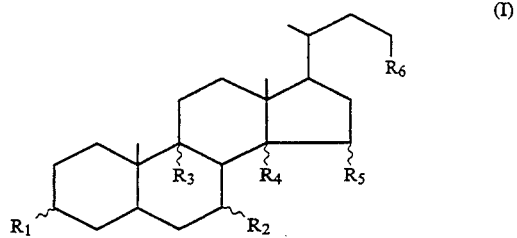

the basic ring structure being saturated or unsaturated, wherein $R_1$ is —OH, =O, —OR$_7$,

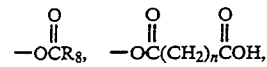

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, (Abstract continued on next page.)

which may be unsaturated or substituted with halogen;

$R_4$ is nonexistent when there is a double bond between the 8 and 14 carbons or $\alpha H$, $\beta H$, or an $\alpha C_1$ to $C_6$ alkyl group;

$R_5$ is $-OH$, $=O$, $=NOH$, or

$-OCR_8$;

$R_6$ is $-CH_2CH(CH_3)_2$ or $CH_2N(CH_3)_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6; and optionally a pharmaceutically acceptable carrier or excipient, with the proviso that $R_6$ is not $-CH_2CH(CH_3)(CH_2OH)$. Methods of using the pharmaceutical compositions containing the side chain derivatized 15-oxygenated sterols are also provided.

A new process is also provided for preparing side chain derivatized 15-oxygenated sterols. This process includes oxidative cleavage of the saturated side chain of the sterol with trifluoroperacetic acid to give a side chain trifluoroacetate and subsequent hydrolysis of this ester. The resultant side chain alcohol is a valuable and advanced intermediate for the preparation of side chain derivatives of 15-oxygenated sterols.

8 Claims, No Drawings

SIDE CHAIN DERIVATIZED 15-OXYGENATED STEROLS, METHODS OF USING THEM AND A PROCESS FOR PREPARING THEM

FIELD OF INVENTION

The present invention relates to side chain derivatized 15-oxygenated sterols and methods for preparing the side chain derivatized 15-oxygenated sterol compounds. The side chain derivatized 15-oxygenated sterol compounds are useful for lowering the activity of HMG-CoA reductase, including all the effects derived from lowering the activity of HMG-CoA reductase. Effects derived from lowering the activity of HMG-CoA reductase include suppression of the biosynthesis of sterols with a resultant reduction in serum cholesterol levels.

BACKGROUND OF THE INVENTION

In many instances, the suppression of biosynthesis of sterols is desirable. For example, it is often desirable to suppress the formation of cholesterol in animals, including humans, whereby the serum cholesterol level in the animal will be lowered.

The concentration of cholesterol in blood serum has been correlated with a number of diseases, particularly atherosclerosis. Atherosclerosis is a condition marked by the formation of plaques in the arterial system. Cholesterol and cholesterol esters are major components of these plaques. While the etiology of the disease is not completely known, it appears that an elevated serum cholesterol level contributes to the development and progression of atherosclerosis.

Cholesterol in animals is derived from two sources, first the intake and absorption of dietary cholesterol and second the biosynthesis of cholesterol from acetate by cells of various organs of the body, e.g., liver, intestines, and skin. The biosynthesis of cholesterol and other sterols from acetate in the body involves a complex sequence of reactions, one of which is the conversion of 3-hydroxy-3-methylglutaryl coenzyme A into mevalonic acid. This reaction is considered to be a major regulation point in the normal biosynthesis of cholesterol in cells. A key regulatory enzyme involved at the level of the enzymatic formation of mevalonic acid is 3-hydroxy-3-methylglutaryl coenzyme A reductase (HMG-CoA reductase). Lowering the activity of HMG-CoA reductase serves to inhibit the biosynthesis of mevalonic acid in cells. If the biosynthesis of mevalonic acid can be inhibited in vivo, production of sterols is reduced, and serum cholesterol levels can thereby be lowered.

Additionally, the growth and proliferation of cells of higher organisms and certain microorganisms, such as yeast and fungi, involve the formation of sterols. Accordingly, inhibition of the biosynthesis of mevalonic acid, and thus reduction of sterol formation, is effective to inhibit the growth of cells, both normal and tumorous. Inhibition of the biosynthesis of sterols also has the effect of inhibiting the growth of certain microorganisms, thereby combatting infections.

In addition to its role in sterol biosynthesis, mevalonic acid is an important precursor of a number of other cell constituents. Thus, while bacteria are generally considered not to need or contain sterols, their growth and proliferation requires synthesis of mevalonic acid and the products derived therefrom. Accordingly, inhibition of mevalonic acid synthesis should inhibit bacterial growth.

It is known from U.S. Pat. No. 4,202,891, which is herein incorporated by reference, that certain 15-oxygenated sterols are effective in the inhibition of the biosynthesis of mevalonic acid and of sterols. A number of desirable side effects can be derived from the inhibition of the biosynthesis of mevalonic acid, including suppressing the formation of cholesterol in animals, whereby serum cholesterol levels may be lowered.

In accordance with the present invention, it has been found that 15-oxygenated sterols in which the saturated side chain has been derivatized are particularly effective to lower the activity of HMG-CoA reductase and, accordingly, to inhibit the biosynthesis of sterols. Additionally, these 15-oxygenated sterols may lower serum cholesterol levels by inhibiting cholesterol biosynthesis, blocking the absorption of cholesterol and/or other mechanisms.

There have been many attempts to derive a facile process whereby the saturated side chains of sterols may be derivatized. These processes, however, have suffered from problems such as low yields and multiple products, making them unsuitable for application to the preparation of side chain derivatized sterols. Of particular interest has been the oxidation of the saturated side chain with trifluoroperacetic acid. See, e.g., Deno and Meyer, *J. Org. Chem.*, 44, 3383–3385, and Takano et al., *Chem. Lett.*, 1265–1266, the disclosures of which are herein incorporated by reference.

SUMMARY OF THE INVENTION

It is an object of the present invention to provide sterols which lower the activity of 3-hydroxy-3-methylglutaryl coenzyme A reductase and lower serum cholesterol.

It is also an object of the present invention to provide a process for the preparation of sterols having 3-hydroxy-3-methylglutaryl coenzyme A reductase lowering activity and serum cholesterol level lowering activity.

In accordance with these and other objects, pharmaceutical compositions are provided for lowering the activity of HMG-CoA reductase and/or lowering serum cholesterol, comprising an amount effective to lower the activity of HMG-CoA reductase and/or lower serum cholesterol of a side chain derivatized 15-oxygenated sterol having the formula (I):

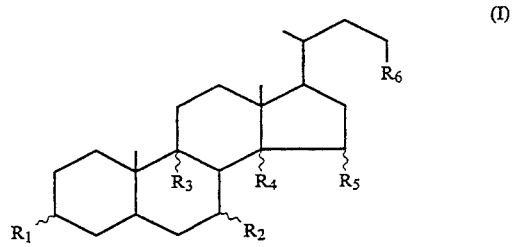

the basic ring structure being saturated or unsaturated, wherein
$R_1$ is —OH, =O, —OR$_7$,

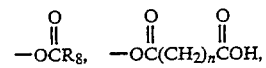

a sulfate group, a sugar moiety, or a Mg, Na, or X salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_4$ is nonexistent when there is a double bond between the 8 and 14 carbons or $\alpha$H, $\beta$H, or an $\alpha C_1$ to $C_6$ alkyl group;

$R_5$ is —OH, =O, =NOH, or

$R_6$ is —CH$_2$CH(CH$_3$)$_2$ or CH$_2$N(CH$_3$)$_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6; and optionally a pharmaceutically acceptable carrier or excipient, with the proviso that $R_6$ is not —CH$_2$CH(CH$_3$)(CH$_2$OH). As used herein "15-oxygenated sterols" refers to sterols having oxygenated functions at the 3 and 15 positions.

Also in accordance with the objects of the present invention, methods of using the pharmaceutical compositions containing the side chain derivatized 15-oxygenated sterols are provided.

A new process is also provided for preparing side chain derivatized 15-oxygenated sterols. This process includes oxidative cleavage of the saturated side chain of the sterol with trifluoroperacetic acid and a strong acid to give a side chain trifluoroacetate and subsequent hydrolysis of this ester. The resultant side chain alcohol is a valuable and advanced intermediate for the preparation of side chain derivatives of 15-oxygenated sterols.

DESCRIPTION OF THE PREFERRED EMBODIMENTS

The present invention relates to 15-oxygenated sterols in which the saturated side chain has been derivatized as inhibitors of sterol biosynthesis. The side chain derivatized 15-oxygenated sterols of the present invention have the formula (I):

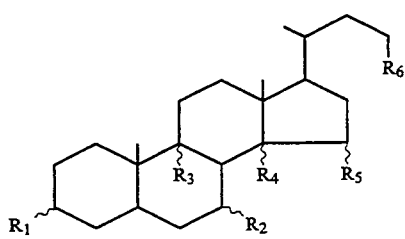

(I)

the basic ring structure being saturated or unsaturated, wherein $R_1$ is —OH, =O, —OR$_7$,

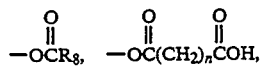

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_4$ is nonexistent when there is a double bond between the 8 and 14 carbons or $\alpha$H, $\beta$H, or an $\alpha C_1$ to $C_6$ alkyl group;

$R_5$ is —OH, =O, =NOH, or

$R_6$ is —CH$_2$CH(CH$_3$)$_2$ or CH$_2$N(CH$_3$)$_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6;

with the proviso that $R_6$ is not —CH$_2$CH(CH$_3$)(CH$_2$OH). It is of course understood that the basic sterol structure may contain substituents that do not adversely effect the properties of the compound at positions other than those of $R_1$, $R_2$, $R_3$, $R_4$, $R_5$, and $R_6$. The basic ring structure may be saturated or unsaturated. For example, there may be unsaturation at one or more of 6(7), 8(14), and 9(11), and, when $R_4$ is alkyl, at 7(8) or 8(9).

When present, the hydrogen at position 5 may be either the $\alpha$ or the $\beta$ position. As used herein,~~~R indicates a substituent in either the $\alpha$ or the $\beta$ position.

Preferred side chain derivatized 15-oxygenated sterols are those having the formula (II):

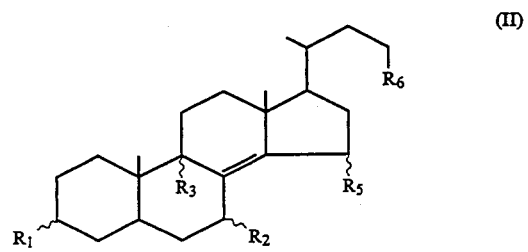

(II)

wherein $R_1$ is —OH, =O, —OR$_7$,

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_5$ is —OH, =O, =NOH, or

$R_6$ is —CH$_2$CH(CH$_3$)$_2$ or CH$_2$N(CH$_3$)$_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6, with the proviso that $R_6$ is not —CH$_2$CH(CH$_3$)(CH$_2$OH).

Preferably, $R_5$ is —OH or =O, more preferably, =O. Preferably, $R_2$ is —H, =O, or $C_1$ to $C_6$ alkyl, more preferably, —H. Preferably, $R_3$ is —H, —OH, or $C_1$ to $C_6$ alkyl, more preferably, —H or —OH. Most preferably, $R_3$ is —H. When $R_2$ and/or $R_3$ are halogen, the halogen is preferably fluorine.

Particularly preferred side chain derivatized 15-oxygenated sterols are 3β,24-dihydroxy-5α-cholest-8(14)-en-15-one, 3β,25-dihydroxy-5α-cholest-8(14)-en-15-one, 3β-hydroxy-5α-cholesta-8(14),24-dien-15-one, 3β-hydroxy-24-dimethylamino-5α-chol-8(14)-en-15-one, and 3β-hydroxy-25,26,26,26,27,27,27-heptafluoro-5α-cholest-8(14)-en-15-one. Most particularly preferred is 3β-hydroxy-25,26,26,26,27,27,27-heptafluoro-5α-cholest-8(14)-en-15-one.

Pharmaceutical compositions containing the side chain derivatized 15-oxygenated sterols of the present invention are useful for lowering the activity of HMG-CoA reductase and thus for inhibiting the biosynthesis of sterols, such as cholesterol. These compositions are also useful for lowering serum cholesterol levels by inhibiting cholesterol biosynthesis, blocking the absorption of cholesterol, and/or other mechanisms. In some cases, these compositions lower serum cholesterol without an adverse effect on food consumption.

The side chain derivatized 15-oxygenated sterols of the present invention may be administered to a host in need thereof either alone or in combination with suitable pharmaceutical carriers and excipients. Suitable administration forms are known to the art and depend primarily on the particular effect sought to be achieved.

Typical administration forms include oral administration forms such as tablets, capsules, powders, granules, and oral solutions. Other administration forms include sublingual, rectal, and buccal administration forms, topical application forms, and parenteral administration forms useful for subcutaneous, intramuscular, or intravenous administration.

The dosage of active side chain derivatized 15-oxygenated sterols necessary to obtain a desired effect is variable over a wide range, depending somewhat upon the particular sterol administered, the effect desired, and the mode of administration. Typically, a suitable dosage is in the range of about 0.1 to about 250 mg per kilogram of body weight per day.

Suitable pharmaceutical carriers which can be used in formulations for administration of the side chain derivatized 15-oxygenated sterols of the present invention are well known in the art. For example, if the compound is to be administered as a solid composition, such as a tablet, the side chain derivatized 15-oxygenated sterol may be mixed with a pharmaceutical vehicle such as gelatin, starch, talc, gum arabic or lactose. Such tablets may be coated with any of the known coatings for pharmaceuticals, according to any of the known techniques, in order to delay disintegration of the pharmaceutical and provide a sustained release.

Capsule preparations may be obtained by mixing the active side chain derivatized 15-oxygenated sterols with an inert pharmaceutical filler or diluent and filling the resultant mixture into a rigid gelatin capsule or into a soft capsule. Preferably, a fatty acid is mixed with the side chain derivatized 15-oxygenated sterols. A syrup or elixir preparation may contain the active side chain derivatized 15-oxygenated sterols together with a sweetening agent, antiseptic compounds, and/or suitable colorings.

Topical preparations may be prepared by mixing the active side chain derivatized 15-oxygenated sterols with suitable salve or ointment bases. Typically such bases are polyvinyl alcohol, waxy polyethylene glycol, or other nontoxic lipophilic agents or vehicles.

A parenteral liquid may be prepared by dissolving or suspending the active ingredient in a sterile liquid vehicle, such as water or brine, a nonvolatile liquid polyethylene glycol, an oil of animal or vegetable origin, or in a mixture of protein, triglycerides, cholesterol, and phospholipids approximating the composition of chylomicrons or other lipoproteins. Parenteral liquids may also advantageously incorporate known lubricants, bactericides, fungicides, stabilizers, tonicity adjusting agents, etc.

The present invention also relates to a process for preparing side chain derivatized 15-oxygenated sterols, which comprises contacting a sterol with a saturated side chain, such as 3β-acetoxy-5α-cholest-8(14)-en-15-one, with trifluoroperacetic acid and a strong acid. Oxidative processes for sterols using peroxy acids, such as trifluoroperacetic acid, are generally known, but suffer from low yields. The present process, however, which employs sterols having an oxygen functionality at C-15, is capable of producing a consistently high yield of a relatively pure product.

The present process, as broadly embodied, involves conversion of a 15-oxygenated sterol, such as a cholest-8(14)-en-15-one, to a side chain trifluoroacetate, such as a 24-trifluoroacetoxychol-8(14)-en-15-one, and subsequent hydrolysis of the trifluoroacetate ester. The side chain free alcohol may then be readily converted to side chain derivatized 15-oxygenated sterols having the ability to lower HMG-CoA reductase activity and lower serum cholesterol levels.

For purposes of the present process, any saturated side chain 15-oxygenated sterol of the formula (III) may be used.

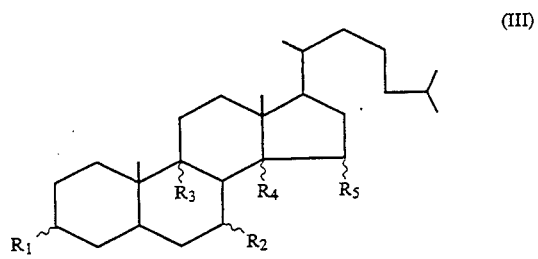

Preferred saturated side chain 15-oxygenated sterols are those having a cholest-8(14)-en-15-one skeleton.

Such sterols are known to the art, and may be readily prepared by the methods disclosed in U.S. Pat. Nos. 4,202,891 and 4,897,475, the disclosures of which are herein incorporated by reference. Preferably, prior to oxidation of the side chain, any reactive functional groups on the sterol, such as a C-3 hydroxy group, are protected with a suitable protecting group, such as acetate.

A particularly preferred saturated side chain 15-oxygenated sterol is 3β-acetoxy-5α-cholest-8(14)-en-15-one.

In accordance with a preferred embodiment of the present invention, a sterol having a cholest-8(14)-en-15-one skeleton, such as 3β-acetoxy-5α-cholest-8(14)-en-15-one is converted to the corresponding 24-hydroxychol-8(14)-en-15-one, such as 3β-acetoxy-24-hydroxy-5α-chol-8(14)-en-15-one, by a process which comprises: (a) contacting the cholest-8(14)-en-15-one with trifluoroperacetic acid and a strong acid for a time sufficient to convert said cholest-8(14)-en-15-one to the corresponding 24-trifluoroacetoxychol-8(14)-en-15-one; and (b) hydrolyzing the 24-trifluoroacetoxychol-8(14)-en-15-one to the 24-hydroxychol-8(14)-en-15-one.

Generally, the preparation of the 24-trifluoroacetate is performed at temperatures below 0° C., preferably below −2° C. The oxidizing agent may be a mixture of trifluoroperacetic acid and a strong acid, or other reagents or mixtures of reagents known to generate peroxy acids in situ. Preferably, the oxidizing agent is a mixture of trifluoroacetic anhydride, a strong acid, and a peroxide. More preferably, the oxidizing agent is a mixture of trifluoroacetic acid, sulfuric acid, and hydrogen peroxide.

This oxidizing agent is known to the art and may be prepared by any of the methods known to the skilled artisan. In accordance with a more preferred embodiment of the present invention, a stirring mixture of trifluoroacetic anhydride and sulfuric acid is cooled to −10° C. and hydrogen peroxide added dropwise over a period of time at a temperature of from −4° C. to −8° C. To this reaction mixture is added in one portion, with vigorous stirring, the cholest-8(14)-en-15-one. The temperature of the reaction mixture is increased to −2° C. and left to stir for ~3.5 hours.

The reaction is quenched by pouring the reaction mixture onto ice and the resultant precipitate recovered, preferably by vacuum filtration. The 24-trifluoroacetate may be used as is or it may be purified by any of the methods known to the art, such as silica gel column chromatography or reversed phase HPLC.

The 24-trifluoroacetoxychol-8(14)-en-15-one can be converted to the 24-hydroxychol-8(14)-en-15-one by any of the methods known in the art for hydrolysis of an ester. Preferably, the ester is removed by reaction with triethylamine and methanol. This reaction may be performed by dissolving the 24-trifluoroacetoxychol-8(14)-en-15-one in a mixture of triethylamine and methanol and allowing the resulting reaction mixture to stir at room temperature, preferably for about 3 hours. The 24-hydroxychol-8(14)-en-15-one is isolated by extraction with an organic solvent, preferably ethyl acetate, which is subsequently removed. The 24-hydroxychol-8(14)-en-15-one product may be purified by any of the methods known to the art, such as column chromatography.

Compounds having a 24-hydroxychol-8(14)-en-15-one skeleton, such as 3β-acetoxy-24-hydroxy-5α-cholest-8(14)-en-15-one, are advanced intermediates in the preparation of side-chain derivatized $\Delta^{8(14)}$-15-ketosterols which lower HMG-CoA reductase activity. The efficient oxidative cleavage of the side chain at C-24 of the readily available starting cholest-8(14)-en-15-one and the facile conversion of the resulting trifluoroacetate to the free alcohol provides this key intermediate in good yield and high purity.

The synthetic protocols to be followed for preparing the preferred side chain derivatized cholest-8(14)-en-15-one compounds are known to those of skill in the art. For example, 3β-acetoxy-24-hydroxy-5α-chol-8(14)-en-15-one is converted to 3β-acetoxy-15-keto-5α-chol-8(14)-en-24-oic acid by oxidation of the alcohol with Jones reagent and subsequent hydrolysis of the C-3 acetate. Compounds such as 3β,24-dihydroxy-5α-cholest-8(14)-en-15-one, 3β,25-dihydroxy-5α-cholest-8(14)-en-15-one and 3β-hydroxy-5α-cholesta-8(14),24-dien-15-one arise from a common intermiediate, viz., 3β-acetoxy-15-keto-5α-chol-8(14)en-24-al. The C-24 aldehyde is readily prepared from 3β-acetoxy-24-hydroxy-5α-chol-8(14)-en-15-one by oxidation with periodinane according to the method of Dess and Martin. Wittig olefination of 3β-acetoxy-15-keto-5α-chol-8(14)en-24-al yields a 24-olefin, 3β-acetoxy-5α-cholesta-8(14),24-dien-15-one which may be hydrolyzed to 3β-hydroxy-5α-cholesta-8(14),24-dien-15-one. Hydration of the 3β-acetoxy-5α-cholesta-8(14),24-dien-15-one and hydrolysis of the ester yields either 3β,24-dihydroxy-5α-cholest-8(14)-en-15-one or 3β,25-dihydroxy-5α-cholest-8(14)-en-15-one, depending upon the reaction conditions selected. For example, oxymercuration of the 24-olefin will result in 3β,25-dihydroxy-5α-cholest-8(14)-en-15-one, while hydroboration will give 3β,24-dihydroxy-5α-cholest-8(14)-en-15-one. The 3β-acetoxy-24-hydroxy-5α-chol-8(14)-en-15-one is converted to 3β-acetoxy-5α-chola-8(14),23-dien-15-one by treatment with ortho-nitrophenyl selenocyanate, followed by hydrogen peroxide. Reaction of this 23-olefin with 2-iodoheptafluoropropane produces 3β-acetoxy-23ξ-iodo-25,26,26,26,27,27,27-heptafluoro-5α-cholest-8(14)-en-15-one. Subsequent reduction with tributyl tin hydride and deprotection of the C-3 alcohol yields the $F_7$ analog of the starting sterol, viz., 3β-hydroxy-25,26,26,26,27,27,27-heptafluoro-5α-cholest-8(14)-en-15-one. Alternatively, the free hydroxy in 3β-acetoxy-24-hydroxy-5α-chol-8(14)-en-15-one may be converted to a leaving group and replaced by nucleophilic substitution. Transformation of 3β-acetoxy-24-hydroxy-5α-chol-8(14)-en-15-one to the C-24 tosylate followed by reaction with dimethylamine and saponification gives the 25-aza analog of the cholest-8(14)-en-15-one, 3β-hydroxy-24-dimethylamino-5α-cholest-8(14)-en-15-one.

The following examples are merely illustrative of the invention and should not be construed as limiting. The examples include preferred embodiments of techniques for preparing the active side chain derivatized cholest-8(14)-en-15-ones. The examples also illustrate the effect of side chain derivatized cholest-8(14)-en-15-ones in lowering the activity of HMG-CoA reductase in cultured mammalian cells and reduction of serum cholesterol levels in rats. One skilled in the art can make, without undue experimentation, various substitutions and variations and by equivalent means, performing in substantially the same manner, obtain substantially the same results without departing from the teaching and spirit of the invention.

EXAMPLE #1

Preparation of 3β-acetoxy-24-hydroxy-5α-chol-8(14)-en-15-one

To a mechanically stirred mixture of trifluoroacetic anydride (100 ml) and sulfuric acid (40.8 ml; 96%) maintained at −10° C. was added a solution of hydrogen peroxide (9.88 ml; 30%) dropwise over a period of 30 min. During the addition, the temperature of the mixture varied from −4° C. to −8° C. 3β-Acetoxy-5α-cholest-8(14)-en-15-one (5.65 g) was, with continued vigorous stirring, added in one portion and the temperature of the reaction mixture was increased to −2° C. Within 1 h the mixture turned to a thick slurry which, with continued vigorous stirring, changed to a clear, light yellow colored, mobile solution after ~3.5 h. TLC (solvent 30% ethyl acetate in hexane) of an ethyl acetate extract of an aliquot of the reaction mixture indicated completion of the reaction as judged by consumption of almost all of the starting material (3β-acetoxy-5α-cholest-8(14)-en-15-one; $R_f$ 0.86) and the presence of a major component with an $R_f$ of 0.67 with minor components with $R_f$ values of 0.60, 0.19, and 0.00.

The reaction mixture was poured onto ice (1000 g), and the resulting white precipitate was collected on a Buchner funnel fitted with polypropylene filter cloth. The solid was dissolved in a mixture (300 ml) of tetrahydrofuran and ethyl acetate (1:4) and passed through a plug of silica gel (30 g) which was then washed with ethyl acetate (600 ml). Evaporation of the solvent under reduced pressure gave a white solid (4.42 g). Reversed phase HPLC (UV detection at 259 nm) showed that the major component corresponded to 3β-acetoxy-24-trifluoroacetoxy-5α-chol-8(14)-en-15-one (83%).

A portion (2.03 g) of the crude product was stirred with a mixture of methanol (50 ml), triethylamine (0.40 ml), and tetrahydrofuran (10 ml) for 1 h at room temperature. Evaporation of the solvent under reduced pressure yielded a white solid (1.80 g) which was applied to a silica gel (34 g; 230–400 mesh) column (2.5 × 30 cm) by the addition of the product preadsorbed on silica gel (5 g; 70–230 mesh). Fractions 22 ml in volume were collected.. The column was successively eluted with 8% ethyl acetate in hexane (500 ml), 16% ethyl acetate in hexane (500 ml), 24% ethyl acetate in hexane (1000 ml) and 28% ethyl acetate in hexane (250 ml), and finally with methanol (150 ml). The chromatography was monitored by TLC and appropriate fractions were pooled and evaporated to dryness under reduced pressure.

The major product (1.554 g), corresponding to an overall yield of 64% from the starting material (3β-acetoxy-5α-cholest-8(14)-en-15-one), was eluted in fractions 51-112 and was characterized as 3β-acetoxy-24-hydroxy-5α-chol-8(14)-en-15-one by its melting point (146.0°-147.5° C.) and by I.R., N.M.R., and M.S. analyses.

EXAMPLE #2

Preparation of 3β-acetoxy-15-keto-5α-chol-8(14)-en-24-oic acid

To 3β-acetoxy-24-hydroxy-5α-chol-8(14)-en-15-one (1.0 g) in acetone (50 ml) an 8N solution of Jones reagent was added dropwise with stirring at room temperature until the orange color of the reagent persisted. 2-Propanol (1 ml) was added, and the reaction mixture was filtered through a sintered glass filter and evaporated to dryness under reduced pressure. The residue was dissolved in ethyl acetate, and the organic solution was washed with water, dried over anhydrous sodium sulfate, and evaporated to dryness under reduced pressure to give 3β-acetoxy-15-keto-5α-chol-8(14)-en-24-oic acid (1.0 g) of over 98% purity as judged by $^1$H NMR. The product showed single component on TLC in three solvent systems (20% methanol in CHCl$_3$, $R_f$ 0.64; isooctaneethyl acetate-acetic acid 5:5:1, $R_f$ 0.56; and CHCl$_3$-acetonemethanol 7:5:1, $R_f$ 0.18. The structure was confirmed by I.R, N.M.R., and M.S. analyses.

EXAMPLE #3

Preparation of 3β-hydroxy-15-keto-5α-chol-8(14)-en-24-oic acid

3β-Acetoxy-15-keto-5α-chol-8(14)-en-24-oic acid (300 mg) and anhydrous K$_2$CO$_3$ (350 mg) in degassed methanol (40 ml) were stirred at room temperature for 5 h under nitrogen in a sealed vial.

After the addition of 1N HCl (6 ml), the mixture was evaporated to dryness under reduced pressure. Ethyl acetate and water were added, and the separated organic phase was washed with water to neutrality. After evaporation of the solvent under reduced pressure, a portion (100 mg) of the crude product (273 mg) was subjected to preparative TLC (Uniplate-T; solvent, 10% acetic acid in CHCl$_3$), and the product (42 mg) was further purified by preparative reversed phase HPLC (solvent, 20% methanol in water) to remove minor impurities. After evaporation of the solvent, the residue was dissolved in 2-propanol and passed through a small column (6 × 90 mm) of Amberlyst (H+) to give, after evaporation of the solvent, 3β-hydroxy-15-keto-5α-chol-8(14)-en-24-oic acid melting at 224°-226° C. The product showed a single component on TLC in three solvent systems (10% acetic acid in CHCl$_3$, $R_f$ 0.83; isooctane-ethyl acetate-acetic acid 5:5:1, $R_f$ 0.41; and hexane-CHCl$_3$-acetic acid 7:2:1, $R_f$ 0.12). The structure was confirmed by I.R., N.M.R., and M.S. analyses.

EXAMPLE #4

Preparation of 3β-acetoxy-15-keto-5α-chol-8(14)-en-24-al

A mixture of 3β-acetoxy-24-hydroxy-5α-chol-8(14)-en-15-one (565 mg; 1.36 mmol) and periodinane (1.26 g; 2.99 mmol) in CH$_2$Cl$_2$ (10 ml) was stirred at room temperature for 3 h under argon. The mixture was diluted with ether (25 ml) and poured into a saturated solution of NaHCO$_3$ (40 ml) containing a seven-fold excess of sodium thiosulfate. After 10 min of occasional swirling, the layers were separated and the organic phase was washed with 10% NaHCO$_3$. The residue (600 mg) obtained upon evaporation of the solvent was subjected to chromatography on a silica gel (10 g) column (15 cm × 1 cm). Using 10% ethyl acetate in hexane as the eluting solvent, fractions 50 ml in volume were collected. The contents of fractions 3-7 were combined and, after evaporation of the solvent, gave 3β-acetoxy-15-keto-5α-chol-8(14)-en-24-al (502 mg; 91% yield) melting at 162°-164° C. The product showed a single component (>99%) on TLC (solvent, 40% ethyl acetate in hexane; $R_f$ 0.63). The structure was confirmed using I.R., N.M.R., and M.S. analyses.

EXAMPLE #5

Preparation of 3β-acetoxy-5α-cholesta-8(14),24-dien-15-one

To a cold slurry (0° C.) of isopropyltriphenylphosphonium iodide (0.839 mg; 1.99 mmol) in anhydrous tetrahydrofuran (5 ml) was added n-butyllithium (1.27 mmol) under argon. The red solution was stirred for 15 min and then added dropwise to a solution of 3β-acetoxy-15-keto-5α-chol-8(14)-24-al (502 mg; 1.21 mmol) in anhydrous tetrahydrofuran (4 ml) at −78° C. After washing of the flask with tetrahydrofuran to ensure a complete transfer of the ylide, the reaction mixture was stirred for 2 h at 0° C. The mixture was poured into water and extracted with ether. The ether solution was washed with water, dried over anhydrous sodium sulfate, and evaporated to dryness under reduced pressure to give a residue (700 mg) which was subjected to chromatography on a silica gel (10 g) column (15 cm × 1 cm). Using 4% ethyl acetate in hexane as the eluting solvent, fractions 50 ml in volume were collected. The contents of fractions 1–6 were combined and, after evaporation of the solvent, gave 3β-acetoxy-5α-cholesta-8(14),24-dien-15-one (400 mg; 71% yield) melting at 129°–130° C. The product showed a single component (>99%) on TLC (solvent, 40% ethyl acetate in hexane; $R_f$ 0.86). The structure was confirmed using I.R., N.M.R., and M.S. analyses.

EXAMPLE #6

Preparation of 3β-hydroxy-5α-cholesta-8(14),24-dien-15-one

To a solution of 3β-acetoxy-5α-cholesta-8(14),24-dien-15-one (150 mg; 0.341 mmol) in a mixture of tetrahydrofuran (1 ml) and methanol (2 ml) was added $K_2CO_3$ (89 mg; 0.65 mmol). After stirring for 4 h at room temperature, the mixture was poured into water and extracted with ether. The residue (141 mg) obtained upon evaporation of the solvent was subjected to chromatography on a silica gel (4.2 g) column (10 cm × 0.8 cm). Using 16% ethyl acetate in hexane as the eluting solvent, fractions 9 ml in volume were collected. The contents of fractions 15–26 were combined and, after evaporation of the solvent, gave 3β-hydroxy-5α-cholesta-8(14),24-dien-15-one (100 mg; 70% yield). Crystallization from methanol gave needles melting at 98°–100° C. The structure was confirmed using I.R., N.M.R., and M.S. analyses.

EXAMPLE #7

Preparation of 3β-acetoxy-25-hydroxy-5α-cholest-8(14)-en-15-one

To a solution of mercuric acetate (147 mg) in a 1:1 mixture (0.6 ml) of tetrahydrofuran and water was added a solution of 3β-acetoxy-5α-cholesta-8(14),24-dien-15-one (131 mg) in tetrahydrofuran (0.6 ml). After stirring at 0° C. for 4 h and then at room temperature for 5 h, 3N NaOH (0.15 ml) was added followed by the addition of sodium borohydride (550 mg) in 3N NaOH (2.5 ml) at 10° C. After 5 min, TLC analysis (solvent, 50% ethyl acetate in hexane) indicated completion of the reaction with a single major component at $R_f$ 0.75. The reaction mixture was poured into water (10 ml) and extracted 3 times with ether (5-ml portions). The combined ether extracts were dried over anhydrous sodium sulfate, and the residue (140 mg) obtained upon evaporation of the solvent was subjected to chromatography on a silica gel column (12.5 cm × 0.8 cm). Using 16% ethyl acetate in hexane as the eluting solvent, fractions 40 ml in volume were collected. The contents of fractions 6–14 were combined and, after evaporation of the solvent, gave 3β-acetoxy-25-hydroxy-5α-cholest-8(14)-en-15-one (119 mg; 87% yield), melting at 151.0°–152.5° C. The structure was confirmed using I.R., N.M.R., and M.S. analyses.

EXAMPLE #8

Preparation of 3β,25-dihydroxy-5α-cholest-8(14)-en-15-one

To a solution of 3β-acetoxy-25-hydroxy-5α-cholest-8(14)-en-15-one (30 mg) in methanol (2 ml) was added potassium carbonate (20 mg). After stirring 4 h at room temperature, TLC analyses (solvent systems, 70% ethyl acetate in hexane and 40% acetone in benzene) indicated completion of the reaction with a single component ($R_f$ values of 0.38 and 0.55 in the 2 solvent systems, respectively). The reaction mixture was poured into water (10 ml) and extracted 3 times with ether (5-ml portions). The combined ether extracts were dried over anhydrous sodium sulfate, and the residue (30 mg) obtained upon evaporation of the solvent was subjected to chromatography on a silica gel (1.5 g) column (6.5 cm × 0.8 cm). The column was eluted with 20% ethyl acetate in hexane (100 ml) followed by 30% ethyl acetate in hexane (40 ml). Fractions 40 ml in volume were collected. The contents of fractions 4–7 were pooled and, after evaporation of solvent, gave 3β,25-dihydroxy-5α-cholest-8(14)-en-15-one (26.6 mg; 98% yield), melting at 177°–179° C. The product showed a single component (>99%) on TLC in two solvent systems (70% ethyl acetate in hexane, $R_f$ 0.38; and 40% acetone in benzene, $R_f$ 0.55). The structure was confirmed using I.R., N.M.R., and M.S. analyses.

EXAMPLE #9

Preparation of 3β,24-dihydroxy-5α-cholest-8(14)-en-15-one

To a solution of 3β-acetoxy-5α-cholesta-8(14),24-dien-15-one (220 mg) in tetrahydrofuran (3 ml) was added boranedimethyl sulfide (0.125 ml) dropwise at 0° C. After standing overnight at −20° C., 3N sodium acetate (0.4 ml) was added followed by 30% aqueous $H_2O_2$ (0.4 ml) at room temperature. After stirring for 3 h at room temperature, the reaction mixture was poured into water (10 ml) and extracted 3 times with ether (5-ml portions). The combined ether extracts were washed with water (5 ml), dried over anhydrous sodium sulfate, and evaporated to dryness. The resulting oily residue was subjected to silica gel column (15 cm × 0.8 cm) chromatography. Using 16% ethyl acetate in hexane as the eluting solvent, fractions 8 ml in volume were collected. The contents of fractions 64–99 were pooled and, after evaporation of the solvent, gave 3β-acetoxy-24-hydroxy-5α-cholest-8(14)-en-15-one (66 mg) as an oil to which, after dissolving in methanol (3 ml), potassium carbonate (40 mg) was added. After stirring for 4 h at room tempeature, TLC analyses (solvent systems, 70% ethyl acetate in hexane and 50% acetone in benzene) indicated completion of the reaction with one major product (with $R_f$ values of 0.51 and 0.27 in the 2 solvent systems, respectively). The reaction mixture was poured into water (10 ml), extracted 3 times with ether (5 ml portions), and the combined ether extracts were dried over anhydrous sodium sulfate and evaporated to dryness. The residue (55 mg) was subjected to chromatography on a silica gel (4 g) column (10 cm × 0.8 cm). Using 30% ethyl acetate in hexane as the eluting solvent, fractions 8 ml in volume were collected. The contents of fractions 11–17 were combined and, after evaporation of the solvent, gave 3β,24-dihydroxy-5α-cholest-8(14)-en-15-one (21 mg; 10% yield). The structure was confirmed by I.R., N.M.R., and M.S. analyses.

EXAMPLE #10

Preparation of 3β-acetoxy-24-tosyloxy-5α-chol-8(14)-en-15-one

A solution of 3β-acetoxy-24-hydroxy-5α-chol-8(14)-en-15-one (400 mg) in dry pyridine (3 ml) and a solution of p-toluenesulfonyl chloride (300 mg) in dry pyridine (2 ml) were cooled in sealed vials in a freezer, combined, and kept at 5° C. in a sealed vial for 24 h. The reaction mixture was poured onto ice and the solid product was collected on a filter and washed with water. Reversed phase HPLC analysis on a Microsorb $C_{18}$ column (solvent, methanol) indicated the following composition: 3β-acetoxy-24-tosyloxy-5α-chol-8(14)-en-15-one, 95%; unreacted 3β-acetoxy-24-hydroxy-5α-chol-8(14)-en-15-one, 3%; and 3β-acetoxy-24-chloro-5α-chol-8(14)-en-15-one, 2%. The crude tosylate (497 mg) was subjected to chromatography on a silica gel (70–230 mesh) column (250 mm × 14 mm). Using 5% ethyl acetate in hexane, fractions 20 ml in volume were collected. At fractions 39 and 77, the eluting solvent was changed to 20% ethyl acetate in hexane and 50% ethyl acetate in hexane, respectively. The contents of fractions 41–74 contained 3β-acetoxy-24-tosyloxy-5α-chol-8(14)-en-15-one (392 mg, 66% yield) with a purity of 99% as judged by HPLC analysis. Additional material (62 mg) of 95% purity was recovered in fractions 75–83. The contents of fractions 41–44 (171 mg) were recrystallized from ether-hexane to give 3β-acetoxy-24-tosyloxy-5α-chol-8(14)-en-15-one (150 mg) melting at 158.0°–159.5° C. The structure was confirmed using I.R., N.M.R., and M.S. analyses.

EXAMPLE #11

Preparation of 3β-acetoxy-24-dimethylamino-5α-chol-8(14)-en-15-one

A solution of the 3β-acetoxy-24-tosyloxy-5α-chol-8(14)-en-15-one (337 mg) in dry dioxane (5 ml) was added to a solution of dimethylamine (240 mg) in dry dioxane (4 ml) in a sealed vial. The dimethylamine solution was prepared by dripping a concentrated aqueous solution of dimethylamine hydrochloride onto KOH pellets and passing the resulting dimethylamine gas through a tube containing Drierite and then into dioxane. After stirring of the reaction mixture at 50° C. for 22 h, analysis by normal phase HPLC on a 5-μm Spherisorb silica column (250 mm × 4.6 mm) showed: 3β-acetoxy-24-dimethylamino-5α-chol-8(14)-en-15-one, 94.8%; unreacted 3β-acetoxy-24-tosyloxy-5α-chol-8(14)-en-15-one, 3.6%; and another impurity, 1.6%. After evaporation of the solvent with a stream of nitrogen, ether and 10% NaOH were added. The ether layer was washed with 10% NaOH and water, and then acidified with 10% HCl. The resulting white precipitate was collected on a filter and, after the addition of 10% NaOH and ether, the ether solution was washed with water, dried over anhydrous sodium sulfate, and evaporated to dryness to give 3β-acetoxy-24-dimethylamino-5α-chol-8(14)-en-15-one as a white solid (165 mg, 63% yield) melting at 122°–124° C.; 99% purity on reversed phase HPLC. The structure was confirmed using I.R., N.M.R., and M.S. analyses.

EXAMPLE #12

Preparation of 3β-hydroxy-24-dimethylamino-5α-chol-8(14)-en-15-one

To a solution of 3β-acetoxy-24-dimethylamino-5α-chol-8(14)-en-15-one (155 mg) in degassed methanol (7.5 ml) was added a solution of LiOH·$H_2O$ (90 mg) in degassed methanol (3.75 ml). After stirring for 5 h at room temperature under nitrogen, the reaction mixture was extracted with ether, and the ether solution was washed with water, dried over anhydrous sodium sulfate, and evaporated to dryness. The resulting white solid (110 mg, 78% yield) was subjected to preparative TLC (Uniplate-T; solvent, hexane-$CHCl_3$-triethylamine, 6:14:1). The major component ($R_f$ 0.48) was recovered from the plate to give 3β-hydroxy-24-dimethylamino-5α-chol-8(14)-en-15-one (71 mg) melting at 160.0°–161.5° C.; 99% purity on normal phase HPLC; single component on TLC in two solvent sysstems (hexane-$CHCl_3$-triethylamine, 6:14:1, $R_f$ 0.22; 20% $CH_3OH$ in $CHCl_3$, $R_f$ 0.17). The structure was confirmed using I.R., N.M.R., and M.S. analyses.

EXAMPLE #13

Preparation of 3β-acetoxy-5α-chola-8(14),23-dien-15-one

To a mixture of 3β-acetoxy-24-hydroxy-5α-chol-8(14)-en-15-one (1.217 g; 2.93 mmol) and ortho-nitrophenyl selenocyanate (0.86 g; 3.8 mol) in a dry round-bottom flask was added tetrahydrofuran (15 ml) under nitrogen. Tributylphosphine (0.95 ml; 3.8 mmol) was added dropwise to the reddish-colored solution over ~2 min. After stirring the blackish-yellow mixture at room temperature for 2 h, the THF was evaporated, and the residue was adsorbed on silica gel (7 g). The resulting solid was passed through a silica gel column (15 cm × 8 mm) using methylene chloride-ethyl acetate-hexane (2:1:7,500 ml) as the eluting solvent. The eluate was evaporated to dryness to give the crude ortho-nitrophenyl selenide (1.8 g). The product showed a single component on TLC (solvent system, 30% ethyl acetate in hexane; $R_f$ 0.51). To the selenide (1.8 g) in tetrahydrofuran (20 ml) was added 30% hydrogen peroxide (1.5 ml) dropwise. After stirring at room temperature for 4 h, tetrahydrofuran was evaporated, and the residue was poured into water (100 ml). The resulting mixture was extracted with ethyl acetate (3 × 20 ml) and washed with aqueous $NaHCO_3$ and water. The residue (1.16 g) obtained upon evaporation of the solvent was passed through silica gel (16 cm × 8 mm) using 4% ethyl acetate in hexane as the solvent. Evaporation of the solvent and recrystallization from methanol gave 3β-acetoxy-5α-chola-8(14),23-dien-15-one (0.85 g; 73% yield); MP, 158.5°–159° C. The product showed a single component (>99%) on TLC in two solvent systems (35% ether in hexane, $R_f$ 0.48; 15% ethyl acetate in hexane, $R_f$ 0.49). The structure was confirmed using I.R., N.M.R., and M.S. analyses.

EXAMPLE #14

Preparation of 3β-acetoxy-23ξ-iodo-25,26,26,26,27,27,27-heptafluoro-5α-cholest-8(14)-en-15-one 3β-Acetoxy-5α-chola-8(14),23-dien-15-one (197 mg; 0.494 mmol) was dissolved in hexane (50 ml) in a round-bottom flask fitted with a septum. 2-Iodoheptafluoropropane (0.14 ml; 0.988 mmol) and triethylborane (1M solution in hexane; 0.1 ml; 0.0988 mmol) were successively added. After 4 h at room temperature, TLC analysis (three developments with 10% ethyl acetate in hexane) showed only trace amounts of starting material. The mixture was passed through a column of silica gel (6 g) using hexane (50 ml) and 5% ethyl acetate in hexane (200 ml) as the eluting solvents. Evaporation of the solvent under reduced pressure gave 3β-acetoxy-23ξ-iodo-25,26,26,26,27,27,27-heptafluoro-5α-cholest-8(14)-en-15-one (310 mg; 90% yield). The product showed a single component on TLC in one solvent system (35% ether in hexane, $R_f$ 0.45) and one major (~95%) component ($R_f$ 0.43) and a minor component ($R_f$ 0.485) in another solvent system (15% ethyl acetate in hexane). The structure was confirmed using I.R., N.M.R., and M.S. analyses.

EXAMPLE #15

Preparation of 3β-acetoxy-25,26,26,26,27,27,27-heptafluoro-5α-cholest-8(14)-en-15-one To a solution of 3β-acetoxy-23ξ-iodo-25,26,26,26,27,27,27-heptafluoro-5α-cholest-8(14)-en-15-one (310 mg; 0.446 mmol) and 2,2'-azobisisobutyronitrile (10 mg) in tetrahydrofuran (4 ml) was added tributyltin hydride (0.15 ml; 0.603 mmol) under argon. After 5 h, water (20 ml) was added and the resulting mixture was extracted twice with ether (10 ml portions). The ether solution was washed with water, dried over anhydrous sodium sulfate, and evaporated to dryness. The residue (300 mg) was subjected to chromatography on a silica gel (6 g) column. Using 4% ethyl acetate in hexane as the eluting solvent, fractions 8 ml in volume were collected. The contents of fractions 20–56 were pooled (227 mg) and recrystallized from methanol to give 3β-acetoxy-25,26,26,26,27,27,27-heptafluoro-5α-cholest-8(14)-en-15-one (211 mg; 83% yield); MP 187°–188° C. The product showed a single component on TLC in one solvent system (35% ether in hexane, $R_f$ 0.45) and one major (~98%) component ($R_f$ 0.45) and a minor component ($R_f$ 0.485) in another solvent system (15% ethyl acetate in hexane). The structure was confirmed by I.R., N.M.R., and M.S. analyses.

EXAMPLE #16

Preparation of 3β-hydroxy-25,26,26,26,27,27,27-heptafluoro-5α-cholest-8(14)-en-15-one A solution of 3β-acetoxy-25,26,26,26,27,27,27-heptafluoro-5α-cholest-8(14)-en-15-one (59 mg) in methanol (4 ml) was stirred with potassium carbonate (30 mg) for 5 h at room temperature. Ethyl acetate (10 ml) and water (20 ml) were added and the resulting mixture was extracted twice with ethyl acetate (25 ml portions). The organic extract was washed with water (10 ml), dried over anhydrous sodium sulfate, and evaporated to dryness. The resulting residue (51 mg) was subjected to chromatography on a silica gel column (3.5 cm×0.8 cm). Using 5% ethyl acetate in hexane (100 ml) and 10% ethyl acetate in hexane (250 ml) as the eluting solvents, fractions 50 ml in volume were collected. The contents of fractions 4–7 were pooled to give, after evaporation of the solvent, 49 mg of material which was then recrystallized from hexane to give 3β-hydroxy-25,26,26,26,27,27,27-heptafluoro-5α-cholest-8(14)-en-15-one (38 mg; 69% yield); MP 177°–179° C. HPLC analyses at 259 nm and 210 nm on a Spherisorb ODS-II column (solvent, 7% methanol in water) showed a single component (>99.8% purity) with a retention time of 6.92 min. GC-MS analysis of the 3β-trimethylsilyl derivative showed a single component. The structure was confirmed by I.R., N.M.R., and M.S. analyses.

EXAMPLE #17

Effects of side chain derivatized 15-oxygenated sterols on HMG-CoA reductase activity in CHO-K1 cells The effects of the sterols on HMG-CoA reductase activity were determined on CHO-K1 cells. The cells were obtained from the American Type Culture Collection (Rockville, Md.). (3RS)-[3-$^{14}$C]HMG-CoA (56 mCi per mmol) and (3RS)-[2-$^3$H]mevalonolactone (176 mCi per mmol) were purchased from Amersham Corporation (Arlington Heights, Ill.). Lux tissue culture plasticware was from Miles Scientific (Elkhart, Ind.). Trypsin was obtained from Gibco Laboratories (Grand Island, N.Y.) and Ham's F12 medium, *Proc. Natl. Acad. Sci. U.S.A.*, 53, 288–293 (1965), and phosphate buffered saline (PBS; KCl, 2.7 mM; KH$_2$PO$_4$, 1.2 mM; NaCl, 137 mM; and Na$_2$HPO$_4$, 8.1 mM) were obtained from Irvine Scientific (Irvine, Calif.). Fetal calf serum was purchased from Whittaker M.A. Bioproducts (Elkhart, Ind.).

For cell culture experiments, the sterols and C$_{24}$ acid were added as ethanolic solutions to Ham's F12 medium supplemented with 5% delipidated fetal calf serum (lipid-deficient medium) and allowed to equilibrate for at least 6 hours at room temperature prior to storage at 4° C. Protein in detergent-solubilized extracts of cultured cells was assayed by the Peterson modification, *Anal. Biochem.*, 83, 346–356, of the method of Lowry et al., *J. Biol. Chem*, 193, 265–275.

The CHO-K1 cells were maintained in Ham's F12 medium supplemented with 5% fetal calf serum (lipid-rich medium) in a humidified atmosphere of 5% CO$_2$-95% air at 37° C. Each experiment was initiated by inoculating 3.75×10 cells into 100-mm dishes containing the lipid-rich medium (10 ml), followed by incubating for 48 hours. The medium was aspirated and, after rinsing the plates with PBS (10 ml), the cells were incubated for 18 hours in lipid-deficient media (10 ml). The cells were then incubated with fresh lipid-deficient media (10 ml) containing various concentrations of the 15-oxygenated sterols (from 0.0 μM to 2.5 μM) for 4 hours. Cells were harvested by scraping, and detergent-solubilized cell preparations were obtained for assay of HMG-CoA reductase activity using the method of Brown, Dana and Goldstein, *J. Biol. Chem*, 249, 789–796. Replicate assays (n=3) were carried out as described by Pinkerton et al., *J. Biol. Chem*, 257, 1929–1936, except that the specific activity of (3RS)-[3-$^{14}$C]HMG-CoA was 20,000 dpm per nmol.

The results are presented in Table 1.

TABLE 1

| Sterol concentration (μM) | HMG-CoA reductase activity (% of control activity) | | | | | |
|---|---|---|---|---|---|---|
| | I | II | III | IV | V | VI |
| 0.0 | 100.0 | 100.0 | 100.0 | 100.0 | 100.0 | 100.0 |
| 0.1 | 88.5 | 60.5 | 66.4 | 63.4 | 87.1 | 68.3 |
| 0.25 | 77.3 | 67.0 | 56.2 | 33.5 | 85.4 | 49.1 |
| 0.5 | 69.9 | 51.1 | 50.2 | 32.2 | 73.3 | 35.6 |
| 1.0 | 65.0 | 40.0 | 34.8 | 34.2 | 53.5 | 29.0 |
| 2.5 | 45.6 | 35.2 | 23.7 | 21.5 | 35.0 | 22.2 |

I 3β-hydroxy-15-keto-5α-chol-8(14)-en-24-oic acid
II 3β-hydroxy-5α-cholesta-8(14),24-dien-15-one
III 3β,25-dihydroxy-5α-cholest-8(14)-en-15-one
IV 3β,24-dihydroxy-5α-cholest-8(14)-en-15-one
V 3β-hydroxy-24-dimethylamino-5α-chol-8(14)-en-15-one
VI 3β-hydroxy-25,26,26,26,27,27,27-heptafluoro-5α-cholest-8(14)-en-15-one

EXAMPLE #18

Effects of dietary administration of side chain derivatized 15-oxygenated sterols to rats Male rats (100–140 g) of the Sprague-Dawley strain were obtained from Harlan Sprague-Dawley (Houston, Tex.) and housed in pairs for 6 days on a light (6:00 AM–6:00 PM)—dark cycle and fed a ground basal diet (Purina Formulab 5008) and water ad libitum. The animals were then divided into groups of 8 animals each, such that the mean values of serum cholesterol and body weight were approximately the same. The animals were then housed individually and were provided diet and water ad libitum. Blood for serum sterol concentrations was obtained at ~8:00 AM from tail vein on days 5 and 9.

The experiment involved administration of 3$\beta$-hydroxy-25,26,26,26,27,27,27-heptafluoro-5$\alpha$-cholest-8(14)-en-15-one ($F_7$-15-ketosterol) in basal diet as utilized previously in Schroepfer et al., *Biochem. Biophys. Res. Commun.*, 78, 1227–233 (1977). 3$\beta$-Hydroxy-25,26,26,26,27,27,27-heptafluoro-5$\alpha$-cholest-8(14)-en-15-one was administered at levels of 0.025%, 0.05%, 0.075, and 0.10% (by weight) in basal diet. Control rats received basal diet containing no added sterol.

Serum cholesterol was measured by two methods. Day 0 levels were determined using a commercial assay kit ("Single Vial"; Boehringer Mannheim Diagnostics, catalog no. 236691). This methodology could not be applied to the determination of serum cholesterol in serum samples of rats treated with 3$\beta$-hydroxy-25,26,26,26,27,27,27-heptafluoro-5$\alpha$-cholest-8(14)-en-15-one due to the presence of another sterol which also acted as a substrate for cholesterol oxidase. Accordingly, cholesterol levels in serum were determined by gas chromatography (GC). Routine capillary GC analyses of sterols in serum were made on a 0.1 $\mu$m $Rt_x$ 1701 column (15 m×0.25 mm ID; 14% cyanopropylphenyl, 86% methyl polysiloxane; Restek Corp., Bellefonte, Pa.). Stigmasterol was used as an internal standard. In addition, recovery of sterol after saponification and extraction was monitored through the use of an internal standard of [7(n)-$^3$H]cholesteryl oleate. Routine saponification of sample (100 $\mu$l) involved treatment with 10% KOH in ethanol (500 $\mu$l) followed by extraction with hexane (3×1.5 ml). After evaporation to dryness under nitrogen, the samples were treated with BSTFA-pyridine (1:1, 200 $\mu$l) for 1 hour at room temperature under nitrogen. After evaporation to dryness under nitrogen, the silylated material was dissolved in hexane (500 $\mu$l) and aliquots (1 $\mu$l) were subjected to GC analysis.

The results are presented in Table 2.

Although preferred embodiments of the invention are described herein in detail, it will be understood by those skilled in the art that variations may be made thereto without departing from the spirit of the invention or the scope of the appended claims.

TABLE 2

| Day | $F_7$-15-Ketosterol (% in diet) | Serum Sterols (mM) Cholesterol | Serum Sterols (mM) $F_7$-Cholesterol |
|---|---|---|---|
| 0 | 0.000 | 2.85 ± 0.07 | — |
|   | 0.025 | 2.86 ± 0.06 | — |
|   | 0.050 | 2.86 ± 0.05 | — |
|   | 0.075 | 2.87 ± 0.05 | — |
|   | 0.100 | 2.92 ± 0.05 | — |
| 5 | 0.000 | 2.60 ± 0.12 | 0.0 ± 0.0 |
|   | 0.025 | 2.02 ± 0.12 | 0.13 ± 0.02 |
|   | 0.050 | 2.06 ± 0.07 | 0.34 ± 0.03 |
|   | 0.075 | 1.76 ± 0.05 | 0.32 ± 0.02 |
|   | 0.100 | 1.97 ± 0.09 | 0.34 ± 0.3 |
| 9 | 0.000 | 2.62 ± 0.06 | 0.0 ± 0.0 |
|   | 0.025 | 2.10 ± 0.10 | 0.17 ± 0.02 |
|   | 0.050 | 1.83 ± 0.07 | 0.32 ± 0.03 |
|   | 0.075 | 1.76 ± 0.12 | 0.39 ± 0.05 |
|   | 0.100 | 1.90 ± 0.10 | 0.44 ± 0.05 |

What is claimed is:

1. A pharmaceutical composition for lowering serum cholesterol levels, comprising an amount effective to lower serum cholesterol levels of a side chain derivatized 15-oxygenated sterol having the formula (I):

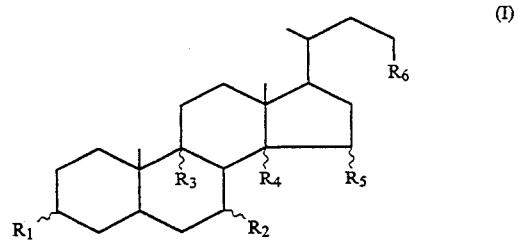

the basic ring structure being saturated or unsaturated, wherein $R_1$ is —OH, =O, —OR$_7$,

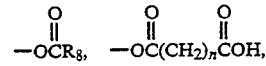

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_4$ is nonexistent when there is a double bond between the 8 and 14 carbons or $\alpha$H, $\beta$H, or an $\alpha C_1$ to $C_6$ alkyl group;

$R_5$ is —OH, =O, =NOH, or

$R_6$ is —CH$_2$CH(CH$_3$)$_2$, in which one or more of the hydrogen atoms is replaced by OH or halogen, —CH=C(CH$_3$)$_2$, in which one or more of the hydrogen atoms may be replaced by OH or halogen, or —CH$_2$N(CH$_3$)$_2$, in which one or more of the hydrogen atoms may be replaced by OH or halogen, provided that no carbon atom with an OH is also substituted with halogen or an additional OH and further provided that no more than three carbon atoms are substituted with an OH;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6; and
optionally a pharmaceutically acceptable carrier or excipient, with the proviso that $R_6$ is not —$CH_2CH(CH_3)(CH_2OH)$.

2. The composition of claim 1, wherein said side chain derivatized 15-oxygenated sterol has the formula (II):

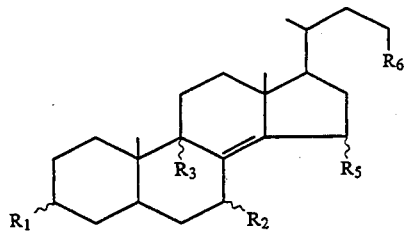

wherein
$R_1$ is —OH, =O, —$OR_7$,

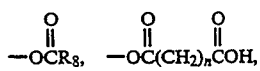

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_5$ is —OH, =O, =NOH, or

$R_6$ is —$CH_2CH(CH_3)_2$ or $CH_2N(CH_3)_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6.

3. The composition of claim 2, wherein said side chain derivatized 15-oxygenated sterol is 3β,24-dihydroxy-5α-cholest-8(14)-en-15-one, 3β,25-dihydroxy-5α-cholest-8(14)-en-15-one, 3β-hydroxy-5α-cholesta-8(14),24-dien-15-one, 3β-hydroxy-24-dimethylamino-5α-chol-8(14)-en-15-one, or 3β-hydroxy-25,26,26,26,27,27,27-heptafluoro-5α-cholest-8(14)-en-15-one.

4. The composition of claim 3, wherein said side chain derivatized 15-oxygenated sterol is 3β-hydroxy-25,26,26,26,27,27,27-heptafluoro-5α-cholest-8(14)-en-15-one.

5. A method of reducing serum cholesterol, which comprises administering to a host in need thereof an amount effective to reduce serum cholesterol of a side chain derivatized 15-oxygenated sterol having the formula (I):

the basic ring structure being saturated or unsaturated, wherein
$R_1$ is —OH, =O, —$OR_7$,

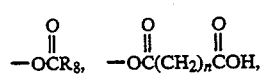

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_4$ is nonexistent when there is a double bond between the 8 and 14 carbons or αH, βH, or an α$C_1$ to $C_6$ alkyl group;

$R_5$ is —OH, =O, =NOH, or

$R_6$ is —$CH_2CH(CH_3)_2$, in which one or more of the hydrogen atoms is replaced by OH or halogen, —$CH=C(CH_3)_2$, in which one more of the hydrogen atoms may be replaced by OH or halogen, or —$CH_2N(CH_3)_2$, in which one or more of the hydrogen atoms may be replaced by OH or halogen, provided that no carbon atom with an OH is also substituted with halogen or an additional OH and further provided that no more than three carbon atoms are substituted with and OH;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6; and optionally a pharmaceutically acceptable carrier or excipient, with the proviso that $R_6$ is not —$CH_2CH(CH_3)(CH_2OH)$.

6. The method of claim 5, wherein said side chain derivatized 15-oxygenated sterol has the formula (II):

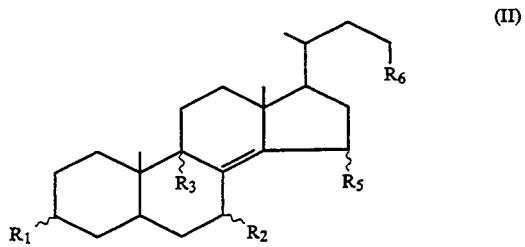

wherein $R_1$ is —OH, =O, —OR$_7$,

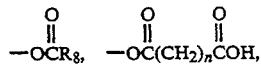

a sulfate group, a sugar moiety, or a Mg, Na, or K salt of a sulfate group;

$R_2$ is —H, —OH, =O, mono- or di-halogen, or a $C_1$ to $C_6$ alkyl group, which may be unsaturated or substituted with halogen;

$R_3$ is —H, —OH, halogen, or a $C_1$ to $C_6$ alkyl group, which may be unsaturated or substituted with halogen;

$R_5$ is —OH, =O, =NOH, or

$R_6$ is —CH$_2$CH(CH$_3$)$_2$ or CH$_2$N(CH$_3$)$_2$, in which one or more of the hydrogen atoms is replaced by OH or halogen;

$R_7$ is a $C_1$ to $C_6$ alkyl group;

$R_8$ is a $C_1$ to $C_{20}$ aliphatic group, which may be substituted or unsubstituted, or a phenyl group; and n is an integer of from 2 to 6.

7. The method of claim 6, wherein said side chain derivatized 15-oxygenated sterol is 3β,24-dihydroxy-5α-cholest-8(14)-en-15-one, 3β,25-dihydroxy-5α-cholest-8(14)-en-15-one, 3β-hydroxy-5α-cholesta-8(14),24-dien-15-one, 3β-hydroxy-24-dimethylamino-5α-chol-8(14)-en-15-one, or 3β-hydroxy-25,26,26,26,27,27,27-heptafluoro-5α-cholest-(14)-en-15-one.

8. The method of claim 7, wherein said side chain derivatized 15-oxygenated sterol is 3β-hydroxy-25,26,26,26,27,27,27-heptafluoro-5α-cholest-8(14)-en-15-one.

* * * * *